United States Patent [19]

Columbus

[11] 4,091,802
[45] May 30, 1978

[54] VENTED LIQUID COLLECTION DEVICE

[75] Inventor: Richard L. Columbus, Rochester, N.Y.

[73] Assignee: Eastman Kodak Company, Rochester, N.Y.

[21] Appl. No.: 658,208

[22] Filed: Feb. 17, 1976

[51] Int. Cl.² .............................................. A61B 5/14
[52] U.S. Cl. ............................ 128/2 F; 128/DIG. 5; 210/83; 210/516; 210/DIG. 23; 233/1 A
[58] Field of Search ................. 128/2 F, DIG. 5; 73/425.4 P; 210/DIG. 23, DIG. 24, 83, 516; 233/1 A

[56] References Cited

U.S. PATENT DOCUMENTS

| 2,369,577 | 2/1945 | Kielland | 235/92 |
|---|---|---|---|
| 2,594,621 | 4/1952 | Derrick | 128/278 |
| 2,737,812 | 3/1956 | Haak | 73/425.4 P |
| 2,779,232 | 1/1957 | Small | 88/14 |
| 2,807,416 | 9/1957 | Parker et al. | 235/92 |
| 2,875,666 | 3/1959 | Parker et al. | 88/14 |
| 2,941,869 | 6/1960 | Brown et al. | 23/253 |
| 3,118,306 | 1/1964 | Sanz | 73/425.4 P |
| 3,433,216 | 3/1969 | Mattson | 128/2 F |
| 3,513,829 | 5/1970 | Deuschle et al. | 128/2 F |
| 3,610,226 | 10/1971 | Albisser | 128/2 F |
| 3,623,475 | 11/1971 | Sanz et al. | 128/2 F |
| 3,640,267 | 2/1972 | Hurtig et al. | 128/2 F |
| 3,645,252 | 2/1972 | Gilford | 128/2 F |
| 3,706,305 | 12/1972 | Berger et al. | 128/2 F |
| 3,706,306 | 12/1972 | Berger et al. | 128/2 F |
| 3,741,732 | 6/1973 | Stanfield | 73/425.4 P |
| 3,785,367 | 1/1974 | Fortin et al. | 128/2 F |
| 3,852,194 | 12/1974 | Zine, Jr. | 210/83 |
| 3,867,923 | 2/1975 | West | 128/2 F |
| 3,901,219 | 8/1975 | Kay | 128/2 F |
| 3,926,521 | 12/1975 | Ginzel | 128/2 F X |
| 3,965,889 | 6/1976 | Sachs | 128/2 F |
| 3,978,846 | 9/1976 | Bailey | 128/2 F |
| 3,983,037 | 9/1976 | Lee et al. | 210/416 R |
| 4,024,857 | 5/1977 | Blecher et al. | 128/2 F |

Primary Examiner—Kyle L. Howell
Attorney, Agent, or Firm—Dana M. Schmidt

[57] ABSTRACT

A collection device wherein fill-augmenting means are provided in a vented collection compartment, whereby rate of collection is increased, and capture means are provided to prevent leakage of the collected liquid out of the vent. The device is particularly useful in the collection and further processing of blood to obtain blood serum for clinical analysis.

18 Claims, 11 Drawing Figures

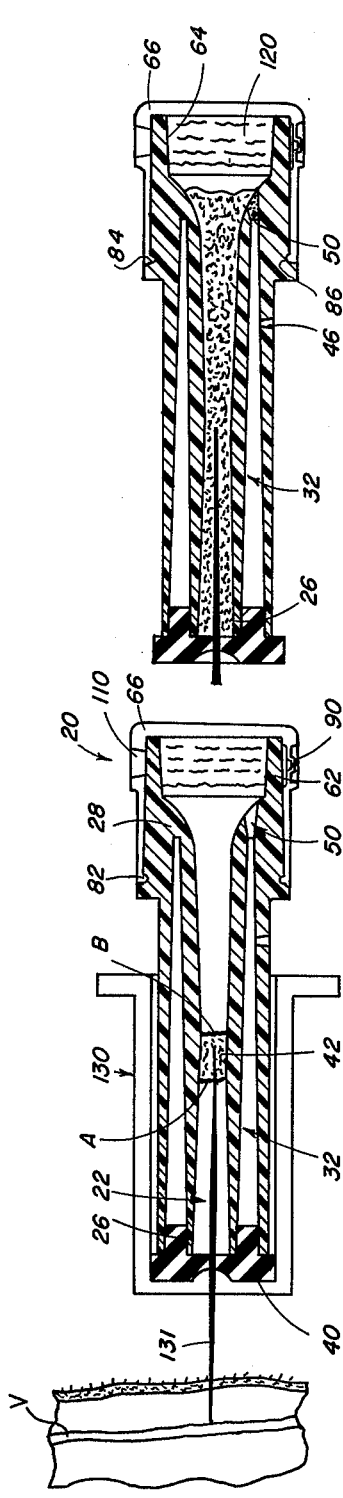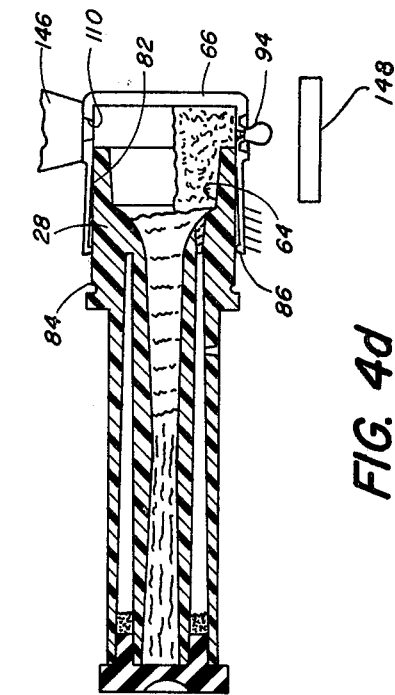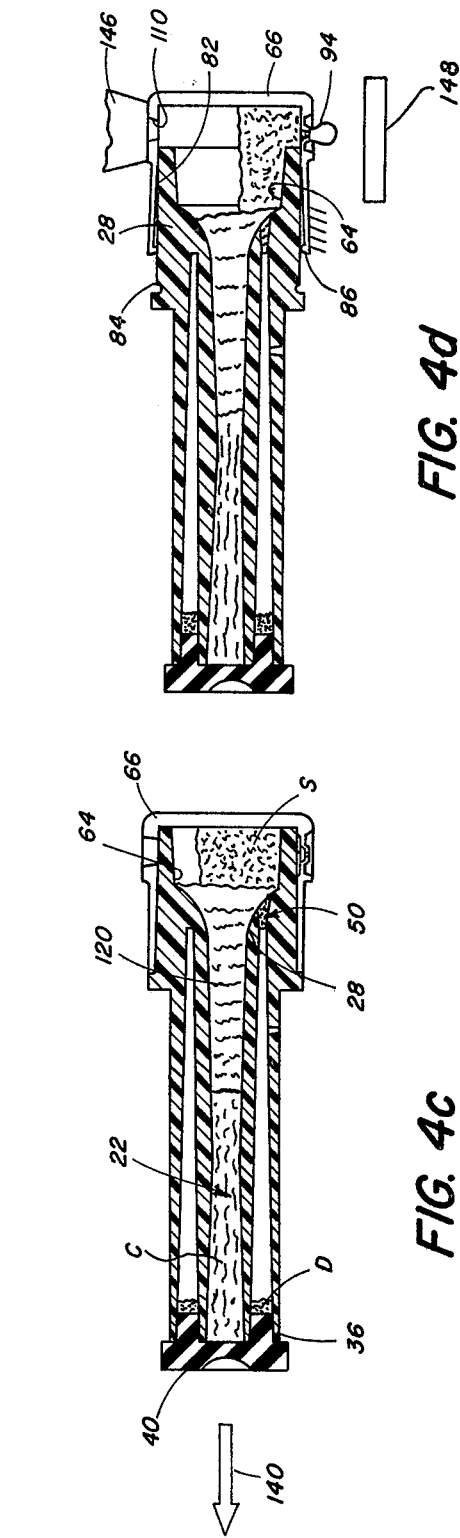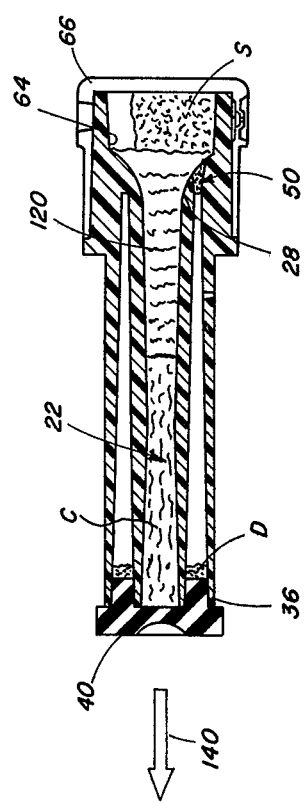

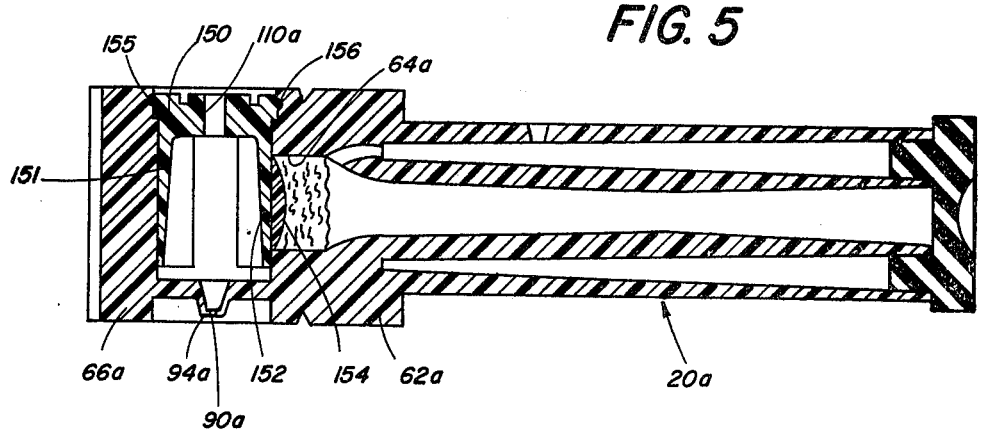
FIG. 5
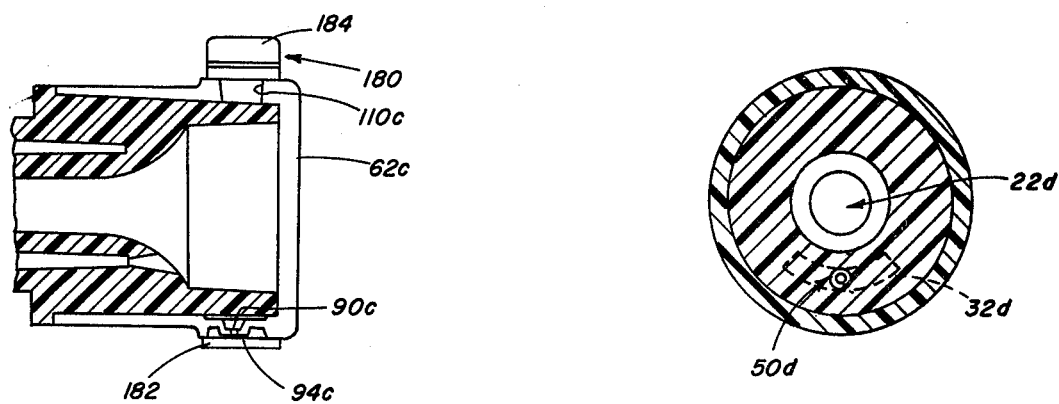
FIG. 6
FIG. 7
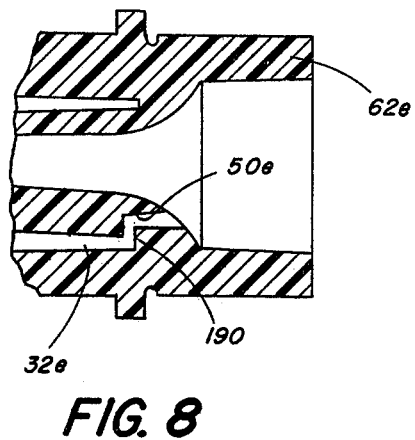
FIG. 8

VENTED LIQUID COLLECTION DEVICE

BACKGROUND OF THE INVENTION

1. Field of the Invention

The invention relates to a device for the collection of liquids, such as whole blood from which serum is to be extracted. The device is vented to the atmosphere and therefore relies primarily on the hydrostatic or other pressure of the liquid being collected to fill the device. The device also has the capability for serum separation and dispensing, following the collection.

2. State of the Prior Art

Of the many devices available to provide blood serum for analysis, the one which has become the norm is the evacuated container. This is simply a partially evacuated glass tube openable at one end except for a septum placed there. One improvement over such an evacuated container which is particularly useful comprises such a glass tube with a movable plug contained within the tube. The plug is preferably a silica gel, with or without a plastic cup-like mandrel positioned with its open end pointed to the septum. By reason of the vacuum, collected blood is easily drawn into the container. The container is then spun about a centrifuge axis adjacent to the septum end, and the gel by reason of its selected specific gravity works up to the serum-cell interface where it plugs the container against remixing of the serum and cells. An example of such a container but without the mandrel is shown in U.S. Pat. No. 3,852,194.

Although such a device is useful in separating the serum from the cells, it has not avoided the transfer difficulties by which the separated serum is obtained. That is, after centrifuging, the serum is commonly poured off into yet another container for the desired clinical testing. All such transfer operations are time consuming, requiring either hand processing or complicated, expensive automatic handling. Furthermore, whenever there is a transfer of a liquid sample to a separate, open container, the sample is aerated and $CO_2$ loss or gain can occur. There is also the danger of improper transfer, either by the use of the wrong container, by the improper patient labeling of the new container, or by both. Still further, contamination of the serum by foreign materials can occur, including for example, contamination by blood cells collected at the septum-container interface prior to centrifuging, a condition known as "blood-ring contamination."

Still other drawbacks concerning evacuated containers are that the rapid intake tends to cause hemolysis by reason of the high shear rate, the vacuum can cause collapse of the patient's vein, and occasionally the containers become "flat," i.e., they lose their vacuum. In such a case of a "flat" container, the broken seal is generally insufficient to create a truly vented configuration, so that the hydrostatic pressure of the veins from which the blood is drawn encounters back pressure, and the rate of fill is insufficient. When the container is formed from solid glass, it is not possible prior to actual use to determine the loss of vacuum merely by visual inspection, and the result is that the patient has to wait while the technician looks for a new, hopefully evacuated, container.

On the other hand, previous vented containers by their nature have been prone to blood spillage, and any spillage or leakage of blood can in turn infect the technician or operator. Furthermore, vented containers generally have not provided the rate of fill characteristic of an evacuated container in which the initial vacuum has been maintained. Thus, vented containers have not been a successful replacement for evacuated containers.

Devices have been developed such as those shown in U.S. Pat. No. 3,433,216, for reusing "flat" blood collection devices. Specifically, the sterilized "flat" collector is placed within an encompassing compartment which is vented and which has a telescoping portion, and a passageway is provided between the two compartments. By closing the vent of the outer compartment, and moving the telescoping portion, a vacuum is thus created, either before or during filling of the collection device. However, the outermost compartment is not designed to function as a blood storage or capture means, and the entire combination makes no provision for a dispensing operation after blood serum separation is complete. Furthermore, there is no provision for a capillary filling of the original blood collection device.

Capillary draws have been used to collect blood, using either one or more simple capillary tubes as in U.S. Pat. No. 3,645,252, or a capillary tube which is connected to and permits flow of the blood into a large container of the type shown, for example, in U.S. Pat. No. 3,640,267. The devices of the latter patent have been designed solely for non-venous collecting, and are not suitable for serum separation in the same container.

Mild obstructions have been placed in blood collecting devices for various purposes other than for creating a capillary effect at the obstruction to fill the container more rapidly. For example, the pipette shown in U.S. Pat. No. 3,741,732 has capillary flow along its entire length, and the obstruction by its hydrophobic nature is designed to terminate rather than assist flow. In the syringe disclosed in U.S. Pat. No. 2,941,869, a coiled wire is disposed in a tube solely to hemolyze the blood flowing past it. Nowhere is capillary flow discussed.

Blood flow devices having capillary restrictions at a portion intermediate the ends thereof have been constructed not for the purpose of collecting blood and for separating serum, but rather for blood cell counting, as shown for example, in U.S. Pat. Nos. 2,369,577; 2,779,232; 2,807,416 and 2,875,666. These devices are not intended for, nor are they capable of, use as serum collectors and separators as there is no provision, for example, for means for controlling flow out of both of the ends of the devices. Instead the flow is commonly gravity or diffusion flow, there being no need to otherwise control it.

Flexible containers have been used to collect whole blood, and by reason of their flexibility, they may have capillary passageways somewhere defined when the walls are collapsed. However, the collapsed wall condition is designed not to fill the containers by capillary action, but rather either to create a vacuum which causes filling of the container, as shown for example in U.S. Pat. No. 3,513,829, or to indicate whether desired arterial blood as opposed to undesired venous blood is being collected, as shown for example in U.S. Pat. No. 3,785,367.

U.S. Pat. No. 3,867,923 is representative of blood collection bags which are completely collapsed along their entire length, and which therefore provide a capillary passageway their entire length. However, such devices lose their effective capillary as soon as blood enters. Because they are not vented to the atmosphere, they require the patient's blood pressure to expand the device into its full volume. No additional means can be applied to assist in the filling of the bag.

Patents relating generally to the background of blood collection include for example U.S. Pat. No. 3,610,226.

RELATED APPLICATIONS

In U.S. application Ser. No. 545,670, filed on Jan. 30, 1975, entitled "Metering Apparatus," there is disclosed a dispenser chamber uniquely designed to dispense microvolume drops, one at a time, of fluids of variable properties such as blood serum. In U.S. application Ser. No. 581,345, filed on May 27, 1975, a CIP of application Ser. No. 539,577 filed on Jan. 8, 1975, entitled "Biological Fluid Dispenser and Separator," there is disclosed a combined serum separator and dispenser which preferably draws in blood at one end and collects and dispenses drops of serum at the other, whereby blood ring contamination can be avoided. The container can be vented or evacuated.

In commonly owned U.S. application Ser. No. 609,121, filed on Aug. 29, 1975 by R. F. Jakubowicz, entitled "Telescoping Serum Separator and Dispenser," there is disclosed a combined serum separator and dispenser wherein the dispensing chamber telescopes with respect to the serum separating compartment to open or close flow of serum from the separating compartment to the dispensing chamber.

OBJECTS OF THE INVENTION

It is a primary object of the invention to provide a collection device suitable for blood collection and for the additional function of serum separation, which, while using a vented container, provides properties similar to evacuated blood collection and serum separation devices, and none of the drawbacks of evacuated containers.

Thus, it is an object of the invention to provide such a vented collection device wherein a portion intermediate the ends of the collection compartment has a fill rate more rapid than conventional vented containers but not so rapid as to cause hemolysis.

It is another object of the invention to provide such a device while preventing operator infection from blood which spills or leaks through the vent.

Yet another object of the invention is to provide such a device wherein the fill rate can further be augmented by use of an external vacuum applied to the vent.

It is a related object of the invention to provide such a device wherein separated serum is automatically displaced during the phase separation step, from the restricted passageway used to collect it.

Other objects and advantages will be apparent upon reference to the following Summary of the Invention and Description of the Preferred Embodiments, when read in light of the attached drawings.

SUMMARY OF THE INVENTION

The invention concerns a liquid collection device, preferably of the vented type, which is suitable for the collection of blood and for subsequent processing, such as centrifuging and dispensing. More specifically, the invention can be considered as an improvement in a device for collecting whole blood, the device comprising 1) an elongated collection compartment defined by opposed side walls extending between two opposed ends, the side walls being spaced apart adjacent to each of the ends by a distance sufficient to preclude capillary flow of blood along the side walls, and 2) means for controlling blood flow out of both of the ends. The improvement comprises either or both a) an overflow storage compartment located adjacent to said collection compartment, said compartments being fluidly connected at one of said ends by an overflow passageway, and b) at a portion intermediate the opposed ends of the collection compartment, fill-augmenting means for providing a withdrawal force on blood deposited from a cannula at that portion.

Alternatively, the invention can be considered as a device for collecting and separating blood serum, comprising a collection and separation compartment having two opposed ends, the compartment being vented to the atmosphere; a phase separator capable of sealing off in the compartment the phase separation between serum and blood cells when blood is centrifuged in the compartment; and capture means positioned adjacent to the compartment for enclosing and collecting excess blood which flows out of the collection and separation compartment by reason of the vent, whereby the excess blood is wholly contained within the device. Further, it can be considered as a liquid collection device comprising two generally elongated compartments concentrically disposed one about the other and a constricted passageway fluidly connecting the compartments, one of the compartments including a capillary passageway for the forceful intake of liquid and the other of the compartments including a vent aperture in fluid communication with the atmosphere.

Still further, the invention can be considered as a vented liquid collection and dispensing device comprising a collection compartment having an intake end, a discharge end opposite to the intake end, and at least one passageway disposed between the ends, a dispensing compartment adjacent the discharge end, a vent passageway extending from the dispensing compartment to the exterior of the device, means for displacing liquid from the collection compartment into the dispensing compartment, and means for sealing off the vent passageway after collection is completed.

BIREF DESCRIPTION OF THE DRAWINGS

FIGS. 4a through 4d are fragmentary elevational views similar to FIG. 1, but illustrating the use of the device to collect, separate, and dispense serum;

FIG. 5 is an elevational view similar to FIG. 1, but illustrating an alternate embodiment;

FIG. 6 is a fragmentary view similar to FIG. 1, but illustrating yet another embodiment; and FIGS. 7 and 8 are fragmentary sectional views similar to FIGS. 2 and 7, respectively, illustrating still other alternate embodiments.

DESCRIPTION OF THE PREFERRED EMBODIMENTS

Although the invention is hereinafter described by reference to its preferred use as a compartment which functions both to collect whole blood and to perform subsequent operations, such as separation of serum from blood cells, it is not limited thereto. Rather, it can be applied to a vented blood collection compartment only, where the intent is to provide rapid filling, the whole blood thereafter being poured off, aspirated, or otherwise removed to a centrifugation chamber for separating the serum. In such a case, a gel separator would not be needed. Further, it can be applied to a compartment for the collection of liquids other than blood wherein features such as positive and rapid fill rates, and non-contamination of personnel, are desired.

As used in this application, terms of orientation such as "up," "down" and the like refer to orientation of parts during actual use.

After the collection, separation and dispensing of blood serum by this device, individual drops of the serum can be deposited for analysis onto a suitable substrate, of which those shown for example in Belgian Patent No. 801,742 granted on Jan. 2, 1974, can be used.

Figure 1:
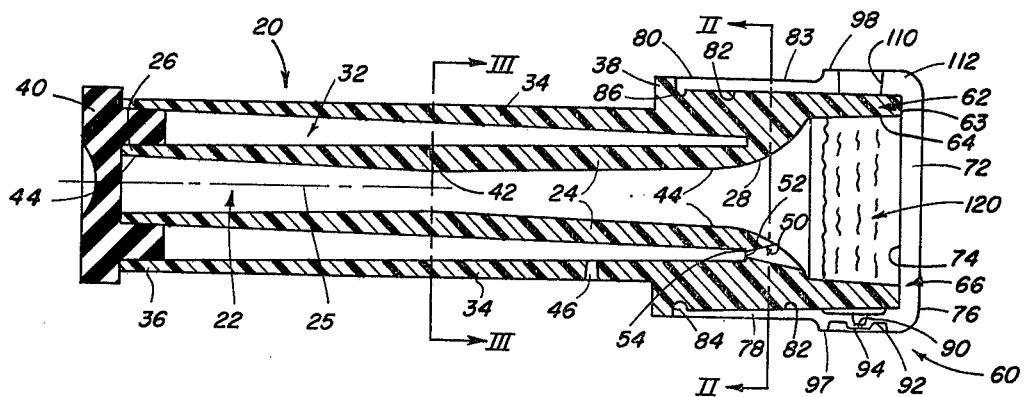
FIG. 1 is an elevational view in section of a device constructed in accordance with the invention.
Figure 2:
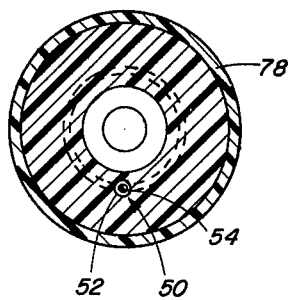
FIGS. 2 and 3 are sectional views taken generally along the lines II—II and III—III, respectively, of FIG. 1.
Figure 3:
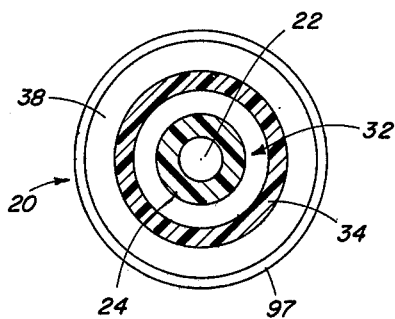

Turning now to FIGS. 1 through 3, a collection device 20 constructed in accordance with the invention comprises two elongated, generally concentrically positioned compartments 22 and 32, an overflow passageway 50 connecting the compartments, and a movable dispenser 60 operatively connected to the innermost compartment 22 and preferably containing a phase separator 120 within the device. The innermost compartment 22 is defined by opposed side walls 24, here shown as a single generally cylindrical wall, symetrically disposed about an axis 25, and terminating at opposed ends 26 and 28. Passageway 50 commences at a point adjacent to end 28 and terminates at an aperture 46. The outermost compartment 32 also is conveniently defined by opposed side walls 34 shown for example as a single cylindrical wall, terminating in opposed ends 36 and 38 and symetrically disposed about axis 25. Ends 28 and 38 preferably are integral extensions of the same wall, as can be achieved by molding device 20 as an integral body. Ends 26 and 36 are provided with means 40 for permitting blood intake as by the penetration of a cannula. Thus the ends 26 and 36 preferably are stoppered by a septum constructed from an elastomer having sufficient elasticity as to permit penetration by the cannula.

In accordance with one aspect of the invention, to augment the fill rate of compartment 22, the walls 24 converge at a portion 42 intermediate the ends 26 and 28 to form a neck which has a maximum dimension transverse to fluid flow at the point of maximum convergence which is no larger than that which will induce capillary flow when blood is deposited by the exit portion of a cannula at portion 42. By reason of this capillary portion, a withdrawal force is delivered on the blood, forcing it into the compartment without the need for pressure being delivered from the patient, until it reaches positions designated as "A" and "B," FIG. 4a, where the capillary effect terminates due to the increased spacing between walls 24. Likewise, the portions 44 of side walls 24 adjacent ends 26 and 28 are spaced farther apart than that which will cause capillary flow adjacent the ends. The ends 26 and 28 lack the capillary effect primarily because in this fashion the desired larger amounts of blood can be collected.

As used herein, "capillary effect" or "capillary flow" refer to the phenomena in which the free surface of the collected liquid, because of surface tension, will move along the confining walls and thus draw in more liquid until a head of liquid is achieved in which gravity prevents further increase in liquid volume, or until the source of liquid is removed.

For whole blood of properties encountered in clinical analysis, a preferred maximum transverse dimension for the capillary effect at portion 42 is about 0.4 cm. The length of portion 42, that is, the distance between points "A" and "B," will vary depending on the amount of taper, and the initial separation at the most constricted portion of the neck. A typical example is about 2 cm.

The location of neck 42 along axis 25 should be selected, therefore, to coincide with the location of the terminus for the cannula. The most common cannula generally in use protrudes about 16 mm into the collection container, as a safety margin, so the neck should be located this distance from end 26 when the device is to be used with such a cannula. Alternatively, a different axial location for neck 42 can be used, provided the length of the cannula is altered accordingly. Still further, successive capillary lengths, not shown, can be disposed along axis 25 to permit the use of the same device 20 for a variety of lengths of cannulae.

Compartment 32 is vented to the atmosphere by passageway 50 and a vent aperture 46, FIG. 1, thus venting both of the compartments so long as passageway 50 is clear of obstructions. Thus, compartment 32 acts as a storage compartment and as capture means for blood which, because of the vented condition, would otherwise spill out of compartment 22. As is described hereinafter, the dispenser 60 is closed during all but the dispensing operation, such that no leakage is possible through that portion. To insure that blood does not further spill out of compartment 32, the vent aperture 46 has an axis which is inclined with respect to flow of liquid in the storage compartment so as to prevent flow out of the aperture. A preferred orientation of the aperture axis is thus generally perpendicular to the axis of centrifugation, for reasons described hereafter.

The particular location of the vent aperture 46 along axis 25 is not critical.

In accordance with still another aspect of the invention, it is preferred that "spilled" blood, i.e., blood which has moved out of compartment 22, not move into the storage compartment until centrifugation, but remain in overflow passageway 50. Further, as described hereinafter, it is preferred once the centrifugation is well underway and the excess blood has moved into compartment 32, that flow out of the compartment via passageway 50 be terminated, in order to permit the dispensing operation. Both of these functions can be satisfied by constructing in passageway 50 a constricted orifice which at its most constricted portion 52 is connected to a shoulder 54 of sharply increased flow dimensions. The effect, when the maximum dimension transverse to flow through the portion 52 is small enough, is to limit flow of the phase separator so that the separator flows into but not completely through the orifice 50, and further to prevent flow of blood beyond portion 52 prior to centrifugation due to the meniscus effect created at the portion 52. It has been determined that the maximum dimension transverse to flow at portion 52 is preferably no greater than about 0.8 mm in order to create the meniscus effect in blood to prevent such flow, and that a further reduction in the maximum transverse dimension to about 0.30 mm is necessary to retain the phase separator. Thus, if the phase separator is used as disclosed, the portion 52 preferably is no larger in such maximum dimension than about 0.30 mm in order to simultaneously achieve both functions. The shoulder 54 should have as its outside, increased dimension, in the case of a 0.30 mm dimension for portion 52, about 0.7 mm.

To mount dispenser 60 used in the dispensing function, the compartment ends 28 and 38 are shaped to form a head 62 which terminates in an end surface 63, the end 28 of compartment 22 being flared out to join with a cavity 64 formed in the head. A sliding container 66 is mounted over the heat 62, and as disclosed in the aforesaid Jakubowicz application, container 66 comprises an end wall 72 having an interior side or surface 74 and an exterior side or surface 76, and opposed side walls 78 extending from side 74, terminating at an opposite end 80 of the container 60. The side walls 78 accommodate or encompass head 62, so that the head is movably mounted and preferably telescoped within end 80 of container 66. A particularly useful configuration is one in which the opposed walls 78 are arranged about an axis which is coincident with axis 25. Thus, as with the other compartments, the walls 78 can have a shape in which the walls form one continuous wall.

The walls 78 have an interior surface 82 and an exterior surface 83. The interior surface 82 preferably matches the shape of head 62. Between the interior surfaces is the interior of the container 66. That interior is temporarily blocked from fluid flow of serum from end 28 of compartment 22 by virtue of the removable seal formed by side 74 of end wall 72 positioned against the surface 63 of head 62. The device 20 is further provided with means for sealing the interior of end 80 of container 66 against head 62 when surface 63 has been blocked by opposite end wall 72, and for slidably moving the container 66 to an open dispensing position. The means permitting the movement of container 66 between the two positions is the approximate coincidence of the interior diameter of surface 82 of container 66 and the exterior diameter of head 62. Flexibility of walls 78 permit a circumferential rim 86 of end 80 to ride across the surface of head 62. A preferred form of the sealing means is a groove 84 extending around the entire circumference of head 62, shaped to mate with rim 86 of end 80. An additional groove, not shown, can be added to head 62 to increase the airtight seal during the dispensing operation, if desired.

Preferably, two apertures 90 and 110 are formed in portions 92 and 112, respectively, of the side walls 78, for the dispensing operation hereinafter described. The portion 92 of the side wall 78 has a specially-constructed drop-forming platform 94 isolated from the rest of the exterior surface 83 by a connecting portion or surface, and surrounded by a protecting shoulder 97. Conveniently, such shoulder 97 is part of a ring 98 extending around the circumference of head 62. Aperture 90 has an exit portion which is centered within the platform 94, and an entrance portion in interior surface 82 of portion 92.

The function of the platform 94 and aperture 90 is to accurately form successive, pendant drops of preditable and uniform volume, each of which is to be touched off on a suitable substrate. To provide this function with a fluid having such drastically varying properties as blood serum, certain features have been found to be useful. Thus, platform 94 is preferably vertically separated from the surface 83 by a minimum distance, and horizontally separated from shoulders 97 by a minimum width. Further, aperture 90 preferably has a maximum dimension at the exterior surface of platform 94, measured transversely to fluid flow therethrough, which is less than that which will permit flow of blood serum under the influence of gravity and which is large enough to retard closure of the aperture by protein agglomeration; the intersection of the aperture 90 with the platform surface preferably is essentially a sharp edge, i.e., having a radius of curvature no greater than about 0.02 cm; and the transition zone between platform 94 and the connecting surface defines an edge which preferably is sufficiently sharp as to prevent the tendency of the serum drop to climb up the connecting surface under the influence of surface tension. The actual values for each of these features of container 66, and other desirable aspects of the dispensing container 66 are disclosed in *Research Disclosure*, Vol. 133, Publication No. 13360, May 1975, the details of which are hereby incorporated by reference.

Aperture 110 in portion 112 of side walls 78 is preferably positioned opposite the aperture 90, and need otherwise be constructed only as a passageway for pressurized gas generated exterior to the container.

Initially disposed within the cavity 64 is the movable phase separator 120. This separator preferably comprises a silica gel which can be a blend of hydrophobic silicon dioxide and a silicone, such as dimethylpolysiloxane, blended to give a thixotropic gel having a specific gravity between about 1.035 and 1.06, and preferably about 1.04–1.05, and a viscosity between about 400 and about 500 poise at a shear rate of about 500 sec.$^{-1}$, and typically 451 poise at 506 sec.$^{-1}$. The gel can be used by itself without a mandrel, as is taught for example in U.S. Pat. No. 3,852,194, or with a mandrel as manufactured for example by Corning Glass Works.

The entire device 20 can be made from any suitable material, of which molded synthetic rigid polymers or "plastics" are useful examples. For example, a rigid "Saran" vinyl chloridevinylidene chloride copolymer manufactured by Dow Chemical Company is one preferred example. At least compartment 22 should be made from a polymer that will be wetted by the collected liquid, such as various polyesters, polystyrene, and various acrylics, or by hydrophobic plastics coated with a surfactant that is nonreactive with the collected liquid.

An appropriate patient identification mark or symbol can be placed or otherwise formed at or on any exterior surface of the device.

Turning now to FIGS. 4a–4d, the use of device 20 is generally as follows: The device is inserted into a conventional syringe 130 having a cannula 131 which, because of the variance in septum sizes and because of the need to puncture the septum 40, extends to the portion 42 of compartment 22. The cannula is inserted into the patient's vein V in a conventional manner, FIG. 4a. Capillary attraction of the blood occurs at portion 42 of walls 24 when the patient's hydrostatic veinal pressure pumps blood into compartment 22.

It has been found that the capillary attraction of the blood at portion 42 provides a faster filling of compartment 22 than if the neck portion 42 were not present. Such more rapid filling provides the readily apparent advantage of reducing the time the patient is subjected to this processing. Because portion 42 is spaced away from the ends 26 and 28, the capillary filling at portion 42 causes blood to flow towards both ends 26 and 28, a slight amount of air being trapped at end 26 as shown in FIG. 4b. During the blood collection, the dispensing container 66 remains closed because of rim 86 seated in groove 84, and gel 120 further assists in sealing off the dispenser from any of the collected blood. However, passageway 50 is clear of obstructions so that most of the initial air of compartment 22 is pumped by the incoming blood into storage compartment 32 via the passageway 50, and thence out vent aperture 46. As shown in FIG. 4b, when the collection is complete, some excess blood normally spills into passageway 50, but the constricted orifice prevents the meniscus from moving past the orifice into the compartment 32. This restriction on blood flow at this stage is preferred because blood in compartment 32 might leak out of aperture 46 due to jarring, gravity, etc.

FIG. 4c illustrates phase separation of the serum during centrifuging. Preferably, device 20 is spun so that the centrifugal force 140 is directed along axis 25 from container 66 towards septum 40. Because the axis of aperture 46 is generally perpendicular to this direction of centrifugal force, the excess blood D preferentially avoids the aperture and flows instead to end 36 of the compartment. The gel 120 moves from its position in cavity 64, FIG. 4b, into compartment 22 adjacent end 28, where it forms a seal separating the serum S, now in cavity 64, from the blood cells C. In doing so, the gel acts as a means for displacing serum from compartment 22 into cavity 64. An additional portion of the gel 120 also flows into passageway 50, where because of constricted portion 52, it remains to form an obstruction, terminating any further flow of liquid. At this point in the processing, device 20 is now ready for dispensing, inasmuch as all portions of compartments 22 and 32 have been sealed off by the phase separator 120.

Dispensing proceeds, FIG. 4d, in the manner described in the aforesaid Jakubowicz application. That is, the container 66 and head 72 are telescoped or otherwise moved away from each other, rim 86 becoming unseated from groove 84. A pressurizing device 146 is positioned over aperture 110, and a selected amount of increased pressure causes a pendant drop to form from platform 94, to be touched off onto a substrate 148. As noted in the Jakubowicz application, to insure that proper drop formation of predictable volume occurs the first time for a given pressure increase resulting from means 146, FIG. 4d, the total air volume above the serum surface should be minimized. Such a feature can be particularly significant where, as here, the air volume is increased drastically before dispensing can be achieved. It has been found that when the air volume above the serum in the container 66 opened to the extended position is about 1300 μl, for example, no problem occurs in accurate dispensing. A typical example of dimensions for device 22 which provide this volume is one in which cavity 64 has an internal diameter of about 0.85 cm, gel 120 substantially fills the flared end 28 after centrifuging; and container 66 has an internal diameter between interior surfaces 82 of about 1.05 cm. In such a case, a typical amount of serum to be dispensed is about 1360 μl.

It will thus be appreciated that container 66 and head 62 cooperate together to provide the means for controlling flow of serum into the dispenser 60. Specifically, they form a shear valve, in which the contracted or closed position, FIG. 4a, results in apertures 90 and 110 being blocked by head 62, from fluid communications with end 28 of compartment 22. This is done without requiring a separate valve part.

Alternatively, however, other forms of dispenser 60 can be used, incorporating a separate valve part, such as those shown in the aforesaid Columbus application Ser. No. 581,345. Specifically, FIG. 5 illustrates such an example, parts similar to those previously described bearing the same reference numeral to which the distinguishing suffix "a" is added. Thus, head 62a of device 20a is modified so as to rigidly define the dispensing container 66a directly fluidly connected to cavity 64a.

Within the dispensing container 66a is mounted a rotating valve 150, having valve legs 151 and 152, leg 152 being provided with a blocking pad 154. Groove 155 permits rim 156 of the valve to rotate, whereby the entire valve can rotate to open or close flow of serum between legs 151 and 152 into the dispensing container. Platform 94a and apertures 90a and 110a are as before except that aperture 110a is in the valve.

FIGS. 6-8 illustrate yet other alternate embodiments. Parts similar to those previously described bear the same reference numerals to which the distinguishing suffixes "c," "d" and "e" are added, respectively.

In FIG. 6, there is illustrated a guard 180 for apertures 90c and 110c, to maintain the apertures free from contamination. That is, aperture 90c if touched by an operator may not properly form drops because of the oils from human skin altering the wettability of the platform 94c. The guard preferably comprises a wrap-around strip 182 completely encompassing and sealing head 62c, having a pull tab 184 and means for assisting in breaking the seal. The seal can be chemical, as by an adhesive, or mechanical, as by heat or ultrasonic vibrations. Specifically, the entire guard can be metallic foil, in which case a fiber should be located under the entire length of the strip to break the seal. Or, it can be all plastic, or a composite in which the tab 184 is plastic while the strip 182 is foil and bridges the tab 184.

FIG. 7 illustrates a storage compartment which is adjacent to, but not concentric with, the collection compartment 22d. Instead, overflow passageway 50d leads into a compartment 32d having a vent aperture, not shown, constructed as described above. The compartment 32d can have any shape, including rectilinear.

FIG. 8 illustrates an overflow passageway 50e in head 62e, from which container 66e has been removed for clarity, wherein the means for terminating flow at the time of serum separation can use a constricted orifice of larger diameter. Specifically, a right-angle turn 190 in the passageway insures some of the gel separator will remain after centrifuging to plug the passageway, even though the flow-through diameter is slightly larger than in the previous embodiments. Although excess blood is not prevented from movement into compartment 32e, prior to centrifuging, by such a construction, blood leakage from the vent aperture can be prevented by adding a porous foam to that aperture, not shown, which will selectively pass air but not a liquid. Also, if foam is used in aperture 50, the size of the orifice at that aperture can be increased, or increased centrifuge force can be used, without destroying the flow terminating effect of the gel seal.

The invention has been described in detail with particular reference to certain preferred embodiments thereof, but it will be understood that variations and modifications can be effected within the spirit and scope of the invention.

What is claimed is:

1. In a device for collecting and separating blood serum and including
    a collection and separation compartment defined by opposed side walls extending between two opposed ends, one of said ends being closed by blood inlet means capable of penetration by a cannula, said side walls being spaced apart adjacent to each of said ends by a distance sufficient to allow non-capillary flow of blood along said side walls, and
    a thixotropic gel phase separator adjacent the other of said ends, said separator being movable in said compartment and adapted for sealing across said compartment the zone of phase separation between serum and blood cells when the blood is centrifuged in said compartment;

the improvement wherein said compartment side walls converge at a portion between said ends to form a neck which is reduced in a dimension transverse to fluid flow therethrough in an amount sufficient to induce capillary flow of blood through the neck, and said device further includes means defining an overflow storage compartment located adjacent to said collection and separation compartment, said compartments being fluidly connected at said other end by an overflow passageway, said passageway including means cooperable with said phase separator for terminating flow therethrough at the time the serum is separated from blood cells by the phase separator.

2. The improved device as defined in claim 1 wherein said flow-terminating means include a constricted portion in said passageway of a dimension which blocks flow of said gel separator during centrifugation.

3. The improved device as defined in claim 2 wherein said constricted portion has a transverse dimension no greater than about 0.30 mm.

4. The improved device as defined in claim 1, and further including means defining a dispensing compartment adjacent said other end and having an outlet aperture and valve means for controlling flow of serum from said collection and separation compartment to said aperture.

5. A device for collecting and separating blood serum, comprising
   means defining a collection and separation compartment having two opposed ends, one of said ends comprising blood inlet means capable of penetration by a cannula;
   a phase separator adjacent the other of said ends, said separator being movable in said compartment and adapted for sealing across said compartment the zone of phase separation between serum and blood cells when blood is centrifuged in the compartment; and
   means defining a storage compartment at least partially surrounding said collection and separation compartment for receiving excess blood which flows out of said collection and separation compartment, and passage means for fluidly connecting said compartments proximate one of said ends;
   said storage compartment having a vent aperture extending directly to the exterior surface of the device.

6. The device as defined in claim 5 wherein said passageway is constructed for cooperation with said separator to terminate flow therethrough at the time the serum is separated from blood cells.

7. The device as defined in claim 6 wherein said passageway includes a constricted orifice and a shoulder adjacent said orifice of sharply increasing flow dimensions, said constricted orifice having a transverse dimension, with respect to the direction of fluid flow, which is sufficiently small to form, in cooperation with said shoulder, a meniscus in blood located in said passageway orifice which resists flow past said shoulder.

8. The device as defined in claim 7 wherein said phase separator is a thixotropic gel and wherein said transverse dimension is no larger than about 0.30 mm, whereby said gel during centrifugation is blocked at said passageway neck.

9. A device for collecting and separating blood serum, comprising
   means defining a collection and separation compartment having two opposed ends, one of said ends being closed and including blood inlet means capable of penetration by a cannula,
   said compartment further including side walls which converge at a portion between said ends to form a neck which is reduced in a dimension transverse to the direction of fluid flow therethrough in an amount sufficient to cause capillary flow of blood through the compartment neck, said compartment neck being sufficiently spaced from both of said ends to allow blood deposited at said neck by a cannula to flow towards each of said ends;
   means defining a vent passageway extending from said compartment to the atmosphere;
   a phase separator adjacent the other of said ends, said separator being movable in said compartment and adapted for sealing across said compartment the zone of phase separation between serum and blood cells when blood is centrifuged in the compartment; and
   means defining a storage compartment located adjacent and in fluid communication with said collection and separation compartment for enclosing and collecting excess blood from said collection and separation compartment.

10. A liquid collection device comprising
    an elongated collection compartment defined by opposed side walls extending between two opposed ends, one of said ends being closed and including blood inlet means capable of penetration by a cannula, said side walls being spaced apart adjacent to each of said ends by a distance sufficient to preclude capillary flow and converging at a portion between said ends to form a neck which is reduced in a dimension transverse to the direction of fluid flow therethrough in an amount sufficient to induce capillary flow of blood through the neck, said neck being sufficiently spaced from both of said ends as to cause blood flowing into said neck to flow towards each of said ends,
    means defining a vent passageway extending from said compartment to the atmosphere;
    and means defining an overflow passageway extending from one of said compartment ends, said passageway including a constricted orifice and a shoulder adjacent said orifice of sharply increasing flow dimensions said constricted orifice having a dimension transverse to the direction of fluid flow that is sufficiently small to form, in cooperation with said shoulder, a meniscus in blood located in said passageway orifice which resists flow past said shoulder.

11. The device as defined in claim 10, and further including a phase separator movable in said compartment and adapted for sealing across said compartment the zone of phase separation between serum and blood cells when the blood is centrifuged within the compartment whereby said compartment functions also as a serum separation compartment.

12. The device as defined in claim 11 wherein said transverse dimension of said orifice blocks flow of said gel during centrifugation.

13. A liquid collection device comprising wall means defining two generally elongated compartments concentrically positioned one about the other; said wall means also defining a control passageway connecting said compartments and comprising a constricted orifice and a shoulder adjacent to the orifice of sharply increased flow dimensions, said constricted orifice having a dimension transverse to the direction of fluid flow that is sufficiently small as to induce, in cooperation with said shoulder, the formation of a meniscus in blood which resists flow past said shoulder, the inner one of said compartments having blood inlet means capable of penetration by a cannula, said wall means further defining a vent aperture extending from the compartment to the exterior of the device, means defining a dispensing chamber located adjacent to said compartments and having an outlet aperture, and valve means for controlling flow of liquid from one of said compartments to said aperture, whereby said device also functions to dispense the liquid.

14. The device as defined in claim 13 wherein said aperture has an axis sufficiently inclined to the flow of liquid in said outermost compartment as to prevent flow of the liquid out of the vent aperture.

15. The device as defined in claim 13 wherein the innermost compartment is defined by side walls which converge at a portion between the ends of the compartment to form a neck of reduced transverse dimension.

16. A liquid collection device comprising wall means defining two generally elongated compartments concentrically disposed one about the other, one of said compartments having blood inlet means capable of penetration by a cannula, and means defining a passageway fluidly connecting said compartments, said innermost compartment including opposed side walls extending between two opposed ends, said side walls being spaced apart adjacent to each of said ends by a distance greater than about 0.4 cm, said side walls converging at a portion intermediate said ends to form a neck having a transverse dimension no greater than about 0.4 cm.

17. A vented liquid collection and dispensing device, comprising means defining a collection compartment, including an intake end permitting liquid intake, a discharge end opposite to said intake end, and at least one capillary passageway disposed between said ends, means defining a dispensing compartment adjacent said discharge end, means defining a vent passageway extending from a point adjacent to said discharge end to the exterior of said device, means for displacing liquid from said collection compartment into said dispensing compartment, and for sealing off said vent passageway, in response to a centrifugal force, said displacing and said sealing means being movably supported within said device and initially disposed adjacent to said discharge end.

18. The device as defined in claim 17 wherein said displacing means and said sealing means comprise a thixotropic gel initially positioned within said dispensing compartment.

* * * * *